(12) United States Patent
Spitzer et al.

(10) Patent No.: US 8,768,477 B2
(45) Date of Patent: Jul. 1, 2014

(54) POST-AURICULAR MUSCLE RESPONSE BASED HEARING PROSTHESIS FITTING

(75) Inventors: Philipp Spitzer, Innsbruck (AT); Stefan Strahl, Innsbruck (AT); Tanja Schulze, Munich (DE); Marek Polak, Innsbruck (AT); Martin Zimmerling, Patsch (AT)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 0 days.

(21) Appl. No.: 13/428,102

(22) Filed: Mar. 23, 2012

(65) Prior Publication Data

US 2012/0245655 A1  Sep. 27, 2012

Related U.S. Application Data

(60) Provisional application No. 61/465,728, filed on Mar. 23, 2011.

(51) Int. Cl.
| | |
|---|---|
| *A61N 1/00* | (2006.01) |
| *A61N 1/36* | (2006.01) |
| *A61B 5/12* | (2006.01) |
| *A61N 1/372* | (2006.01) |
| *A61B 5/0488* | (2006.01) |
| *A61B 5/0484* | (2006.01) |

(52) U.S. Cl.
CPC ............ *A61B 5/125* (2013.01); *A61B 5/0488* (2013.01); *A61N 1/36032* (2013.01); *A61B 5/04845* (2013.01); *A61N 1/37235* (2013.01)
USPC .................................. 607/57; 607/55; 607/56

(58) Field of Classification Search
USPC ....................................................... 607/55–57
See application file for complete search history.

(56) References Cited

U.S. PATENT DOCUMENTS 6,157,861 A * 12/2000 Faltys et al. ..................... 607/57
6,415,185 B1 * 7/2002 Maltan ............................ 607/57

OTHER PUBLICATIONS

Matas et al, Post-auricular muscle reflex in the Middle Latency Evoked Auditory Response, 2009, Braz J Otorhinolayngol., 75(4), pp. 579-585.*

* cited by examiner

*Primary Examiner* — Michael Kahelin
*Assistant Examiner* — Mallika D Fairchild
(74) *Attorney, Agent, or Firm* — Sunstein Kann Murphy & Timbers LLP (57) ABSTRACT

An arrangement is described for fitting a hearing prosthesis system to a prosthesis patient. The PAMR measurement determines a post-auricular muscle reflex (PAMR) response of the patient to an auditory stimulus signal. For example, the PAMR response may include a PAMR amplitude growth function or a PAMR threshold stimulus level at which a PAMR is measured in the patient. Then a patient fitting module sets an operating characteristic of the hearing prosthesis system based on the PAMR response.

19 Claims, 10 Drawing Sheets

(4 of 10 Drawing Sheet(s) Filed in Color)

POST-AURICULAR MUSCLE RESPONSE BASED HEARING PROSTHESIS FITTING

This application claims priority from U.S. Provisional Application 61/465,728, filed Mar. 23, 2011, which is incorporated herein by reference.

TECHNICAL FIELD

The present invention relates to hearing prosthesis systems such as cochlear implant systems, and more specifically to fit customization in such systems.

BACKGROUND ART

Figure 1:
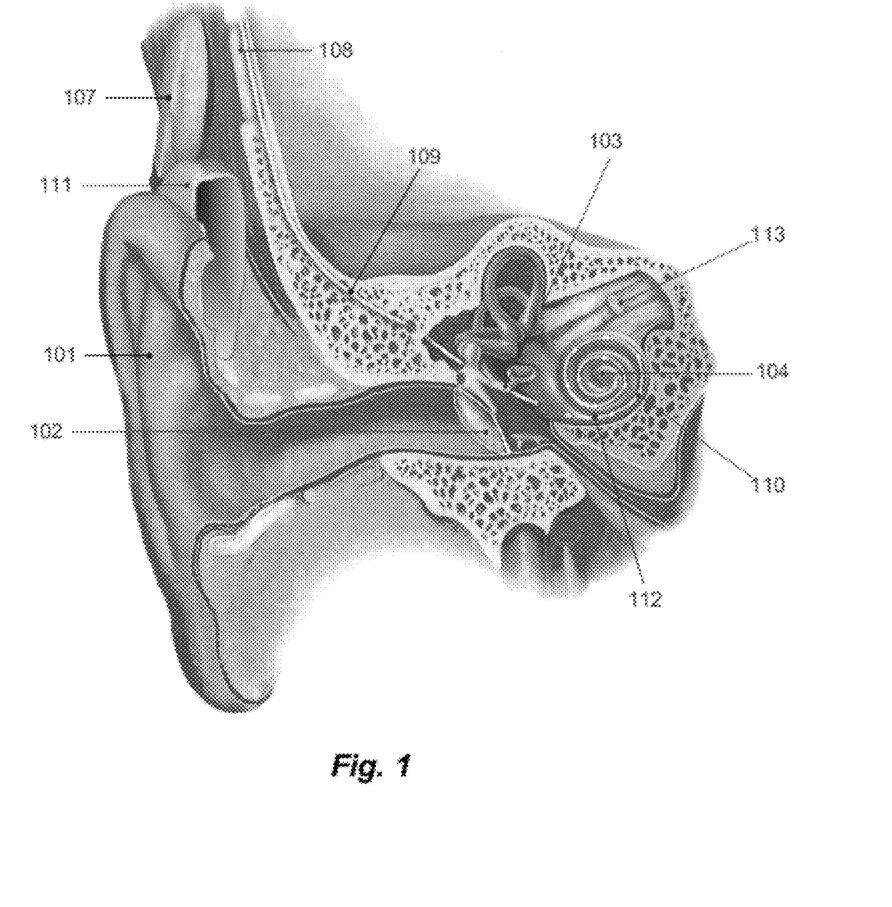
FIG. 1 shows anatomical structures of a human ear having a cochlear implant system.

Most sounds are transmitted in a normal ear as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrodes on its surface that provide selective stimulation of the cochlea 104.

Cochlear implant systems employ stimulation strategies that provide high-rate pulsatile stimuli in multi-channel electrode arrays. One specific example is the "Continuous Interleaved Sampling (CIS)"—strategy, as described by Wilson et al., *Better Speech Recognition With Cochlear Implants*, Nature, vol. 352:236-238 (1991), which is incorporated herein by reference. For CIS, symmetrical biphasic current pulses are used, which are strictly non-overlapping in time. The rate per channel typically is higher than 800 pulses/sec. Other stimulation strategies may be based on simultaneous activation of electrode currents. These approaches have proven to be successful in giving high levels of speech recognition.

Following surgical implantation, the cochlear implant (CI) must be custom fit to optimize its operation with the specific patient user. For the fitting process, it is important to know if an audible percept is elicited and how loud the percept is. Normally this information is gained using behavioral measures. For example, for each electrode contact the CI user is asked at what stimulation level the first audible percept is perceived (hearing threshold (THR)) and at what stimulation level the percept is too loud (maximum comfort level (MCL)). For CI users with limited auditory experiences or insufficient communication abilities (e.g., small children), these fitting parameters can be determined using objective measures.

One commonly used objective measure is the electrically evoked compound action potential (eCAP) which can be easily measured, but shows weak correlations with the MCL ($r=0.57$) and THR ($r=0.55$). See, for example, Miller et al., *The Clinical Application Of Potentials Evoked From The Peripheral Auditory System*, Hearing Research, 242(1-2), 184-197 (2008); incorporated herein by reference.

The electrically evoked stapedius reflex (eSRT) shows high correlations with the MCL. See, for example, Stephan, K. & Welzl-Müller, K., *Post-Operative Stapedius Reflex Tests With Simultaneous Loudness Scaling In Patients Supplied With Cochlear Implants*, Audiology, 39, 13-18 (2000) ($r=0.92$); and Polak, M.; Hodges, A. & Balkany, T *ECAP, ESR and Subjective Levels For Two Different Nucleus 24 Electrode Arrays*, Otology & Neurotology, 2005, 26, 639-645, ($r=0.93$-$0.95$); both incorporated herein by reference. But the eSRT is difficult to measure reliably, for example, movement artifacts of the impedance probe can introduce measurement artifacts.

The electrically evoked auditory brainstem response (eABR) can be measured with a slight expenditure of time, but shows only weak correlations with the MCL ($r=0.54$) and THR ($r=0.69$). See, for example, Brown et al., *Relationship Between EABR Thresholds And Levels Used To Program The Clarion Speech Processor*, Ann Otol Rhinol Laryngol, 108, 50-57 (1999); incorporated herein by reference.

The electrically evoked middle latency response (eMLR) also can be measured with a slight expenditure of time. But the eMLR can only be detected in 35% of awake children at initial device stimulation and 100% detectability is achieved after at least one year. See, for example, Gordon et al., *Effects Of Cochlear Implant Use On The Electrically Evoked Middle Latency Response In Children*, Hearing Research, 204(1-2), 78-89 (2005); incorporated herein by reference.

It is summarized in Miller et al. (2008) that "clinically useful correlations have not been observed in larger populations of CI users for either eCAP or eABR measures." An eSRT based fitting is rarely done as it involves increased costs, for example often a second person is present to guarantee a sufficient sealed microphone probe in the CI user, especially for children. The eMLR can be measured only in a third of CI users at the initial device stimulation. U.S. Pat. No. 6,415,185 describes using a myogenic-based response for fitting CI users.

SUMMARY

Embodiments of the present invention are directed to arrangement for fitting a hearing prosthesis system to a prosthesis patient. The arrangement determines a post-auricular muscle reflex (PAMR) response of the patient to an auditory stimulus signal. For example, the PAMR response may include a PAMR amplitude growth function (input-output function) or a PAMR threshold stimulus level at which a PAMR is measured in the patient. Then an operating characteristic of the hearing prosthesis system is set based on the PAMR response. For example, the operating characteristic may include the definition of the output compression functions ("maplaws") based on the PAMR amplitude growth function. Or the operating characteristic may include the definition of the minimal and maximal stimulation amplitude based on a PAMR threshold stimulus level at which a PAMR is measured in the patient. As used herein, the term "auditory stimulus" generally refers to any type of signal stimulus to the auditory system of the brain including without limitation acoustic, electric, vibrational and optical stimuli.

Determining a PAMR response may be based on an iterative stimulus process, an external bio-signal acquisition system, on an internal fit module in an implanted stimulation processor, and/or an artifact reduction algorithm. Determining a PAMR response may include using a permuted stimulus level to account for bias related to slowly varying muscle tonicity, applying an electrical stimulus signal to the post-auricular muscle before the PAMR is measured to increase the post-auricular muscle tonicity, and/or applying an electrical stimulus signal to an afferent neural structure of the post-auricular muscle before the PAMR is measured to increase the post-auricular muscle tonicity.

The PAMR response may be determined on one side, either ipsilateral or contra-lateral, of the patient, or on both sides of the patient. To increase the post-auricular muscle tonicity the PAMR response may be determined during a controlled post-auricular muscle contraction of the patient user such as the prosthesis patient performs a controlled jaw movement; sucking action; turning the head to the side; opening mouth; positioning head so that the chin of the prosthesis patient is positioned against their chest.

The hearing prosthesis system may include a cochlear implant (CI) system, in which case the operating characteristic may be associated with an electrode contact in an implanted electrode array and the PAMR response may be determined from multiple electrode contacts in the array. The hearing prosthesis system may include an auditory brainstem implant (ABI) system, an Electric Acoustic Stimulation (EAS) system, a middle ear implant (MEI) system, a bone-conductive device system, a conventional hearing aid (HA) system, or an optical hearing prosthesis system.

In specific embodiments, the fitting of the hearing implant system could combine PAMR recording results from different electrodes, combinations of PAMR results with other objective or subjective results, and/or by including already recorded data. The specific form of the auditory stimulus signal includes single pulses on single electrodes, single pulses on multiple electrodes, signal bursts on single or multiple electrodes, combined electric and acoustic stimulus signals, and stimulus signals using a speech coding strategy, speech signals, speech-like signals, and/or music signals.

Embodiments of the present invention also include an implant fitting arrangement for fitting a hearing prosthesis system to a prosthesis patient using a method according to any of the foregoing.

Embodiments of the present invention also include a computer program product implemented in a tangible computer readable storage medium for fitting a hearing prosthesis system to a prosthesis patient. The product includes program code for fitting the system using a method according to any of the foregoing.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

The post-auricular muscle reflex (PAMR) is a large myogenic response that occurs between about 10 and 25 ms after an acoustic stimulus. It has been reported that the PAMR threshold shows a high correlation with pure-tone average thresholds in normal hearing subjects and in subjects with sensorineural hearing loss using an acoustic stimulation. (r=0.82 at 2 kHz) Purdy et al., *The Post-Auricular Muscle Response: An Objective Electrophysiological Method For Evaluating Hearing Sensitivity*, Int J Audiol, National Acoustic Laboratories, Sydney, NSW, Australia, 2005, 44, 625-630; incorporated herein by reference. Purdy reported that PAMR can be reliably measured (>90%) when the eyes are turned towards the recording site. This reflects an increased PAM tonicity which can be explained by the Wilson's oculoauricular phenomenon which associates ear movements with lateral eye movements.

It is believed that the afferent pathway responsible for the PAMR includes the ventral cochlear nucleus, superior olivary nucleus and the lateral lemniscus nucleus and either the inferior colliculus or the reticular formation. The efferent pathway is along the facial nerve to the PAM. See, for example, Patuzzi, R. B. & O'Beirne, G. A., *A Correlation Method For Detecting The Sound-Evoked Post-Auricular Muscle Response (PAMR)*, Hear Res, 138, 147-162 (1999); Patuzzi, R. B. & O'Beirne, G. A. *Effects Of Eye Rotation On The Sound-Evoked Post-Auricular Muscle Response (PAMR)*, Hear Res, 138, 133-146 (1999); both incorporated herein by reference.

It has been shown that the PAMR can be recorded at threshold levels in normal-hearing and hearing-impaired listeners with a mean difference of 9 dB between the PAMR threshold and the 2 kHz audiometric threshold. It has further been shown that using optimal recording and stimulus settings the PAMR can be reliably recorded in most adults. However, no one has ever proposed a PAMR-based patient fitting algorithm for a hearing prosthesis system such as a cochlear implant (CI).

Various embodiments of the present invention are directed to patient fitting of a hearing prosthesis based on generating and measuring the post-auricular muscle response (PAMR). In addition to patient fitting, such an arrangement may also be useful for testing the functionality of the hearing prosthesis system, and to acquire an intra-operative and/or post-operative confirmation of a correct electrode placement.

As the origin of the post-auricular muscle reflex is similar to the stapedius muscle reflex, it is expected to show higher correlations with the desired fitting parameters than eCAP or eABR recordings. Furthermore, the eSRT measurement normally results in a single threshold value—the highest stimulation level at which no muscle contraction response is obtained. This is due the fact that the stimulation threshold for the eSRT response is near the MCL so that eSRT responses can only be measured over a small stimulation range. In contrast, PAMR measurements normally result in an input-output function with increasing PAMR responses for increasing stimulation amplitudes (e.g. FIG. 8). In other words, as the PAMR is already elicited at low stimulation levels, this measurement has the potential to cover a large dynamic range for each electrode. Thereby PAMR responses can quantitatively be evaluated similar to eCAP or eABR measurements, for example the slope of the I/O function or the latencies of the PAMR waveform at different stimulation amplitudes can be analyzed.

Thus embodiments of the present invention are directed to arrangements for fitting a hearing prosthesis system to a prosthesis patient based on determining a post-auricular muscle reflex (PAMR) response of the patient to an auditory stimulus signal. For example, the PAMR response may include a PAMR amplitude growth function (input-output function) or a PAMR threshold stimulus level at which a PAMR is measured in the patient. Then an operating characteristic of the hearing prosthesis system is set based on the PAMR response. For example, the operating characteristic may include the definition of the output compression functions ("maplaws") based on the PAMR amplitude growth function. Or the operating characteristic may include the definition of the minimal and maximal stimulation amplitude based on a PAMR threshold stimulus level at which a PAMR is measured in the patient.

In specific embodiments, a PAMR measurement module could combine PAMR recording results from different electrodes. For example, a shift, scale and tilt of the profile could be performed as discussed Botros, A. & Psarros, C., *Neural Response Telemetry Reconsidered: I. The Relevance of ECAP Threshold Profiles and Scaled Profiles to Cochlear Implant Fitting*, Ear and Hearing, 31, 367-379 (2010); incorporated herein by reference. Similarly, a patient fitting module of the hearing implant system could make use of combinations of PAMR results with other objective or subjective results such as is described in U.S. patent application Ser. No. 12/890,188, filed Sep. 24, 2010, incorporated herein by reference. And the recording of PAMR responses could be accelerated by including already recorded data (e.g. thresholds from adjacent electrodes).

The specific form of the auditory stimulus signal includes single pulses on single electrodes, single pulses on multiple electrodes (parallel stimulation), signal bursts on single or multiple electrodes, combined electric and acoustic stimulus signals, and stimulus signals using a speech coding strategy (for example, a speech coding strategy that will be used later in normal system operation), and more generally speech signals, speech-like signals, and/or music signals.

Figure 2:
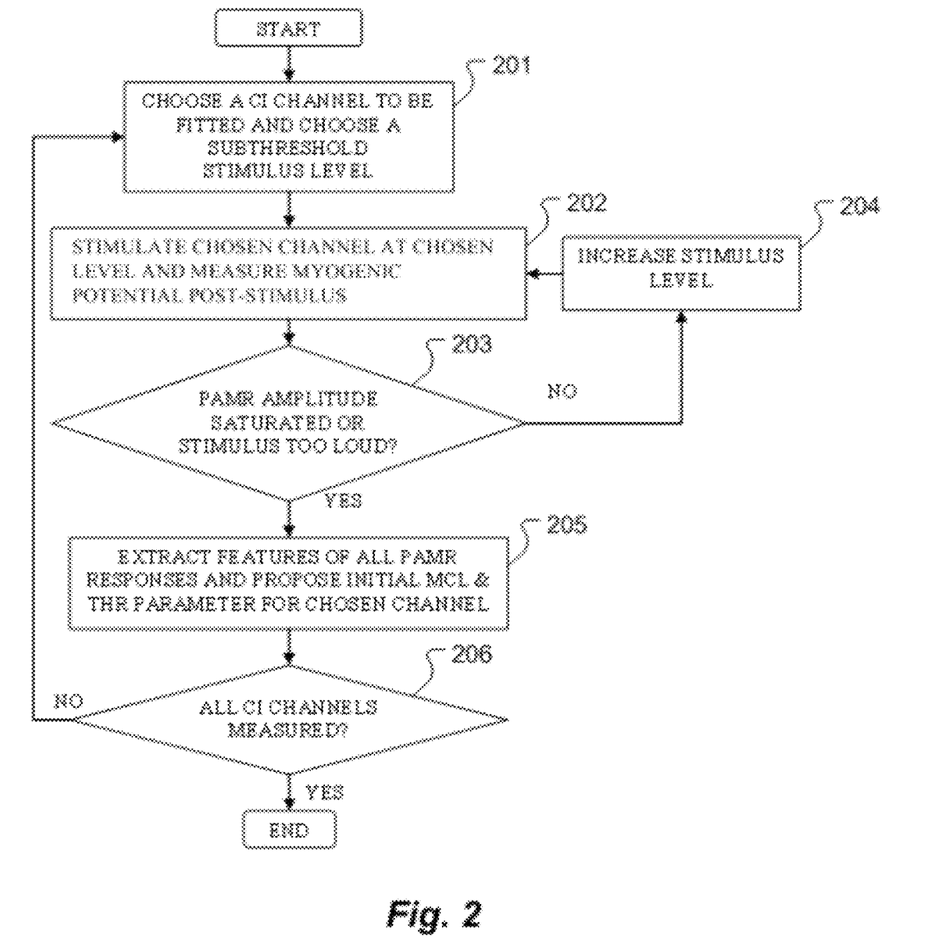
FIG. 2 shows various logical steps in a PAMR-based patient fit process according to one embodiment of the present invention.

FIG. 2 shows an example of a PAMR-based amplitude growth-based fitting procedure. The goal is to determine the lowest stimulation level that elicits an audible percept (THR) and the highest still comfortable stimulation level (MCL). First, the PAMR measurement module selects an initial electrode channel to be fit, step 201. In an iterative process, the PAMR measurement module then stimulates the current electrode channel at the chosen stimulus level and the myogenic potential is measured and recorded post-stimulus, step 202. The initial stimulation level should be sub-threshold (e.g. 0 µA) and if no PAMR response is measured and the stimulus level is still below the user's MCL, step 203, the PAMR measurement module increases the stimulus level, step 204 and repeats the measurement, step 202, until either the PAMR response is saturated or the stimulus level reaches the user's MCL, step 203.

Using the stimulation level at which the first PAMR response was observable (PAMR-THR), the slope of the amplitude growth function (PAMR-SLOPE), the maximal PAMR response (PAMR-MAX) together with PAMR waveform features for the N applied stimulation levels $L_1, \ldots, L_N$ like the latency of the peaks (PAMR-P1($L_1$), PAMR-N1($L_1$), . . . ) the fitting functions THR=$f_\tau$(PAMR-THR, PAMR-SLOPE, PAMR-MAX, PAMR-P1($L_1$), . . . , PAMR-P1($L_N$), PAMR-N1($L_1$), . . . ) and MCL=$f_{s2}$ (PAMR-THR, PAMR-SLOPE, PAMR-MAX, PAMR-P1($L_1$), . . . , PAMR-P1($L_N$), PAMR-N1($L_1$), . . . ) can be approximated by the PAMR measurement module, step 205. This may involve using, for example, a spline interpolation technique (see, for example Bojanov et al., *Spline Functions and Multivariate Interpolations*, Kluwer Academic Publishers, Dordrecht/Boston/London, 1993; incorporated herein by reference). Or the PAMR measurement module may make a determination of the THR as PAMR-THR times some fit factor x and MCL as PAMR-THR times some fit factor y may be sufficient for some embodiments. An alternative approach would be to estimate the THR and MCL using a single PAMR waveform feature, for example THR=$k_\tau$*PAMR-SLOPE and MCL=$k_\mu$*PAMR-THR where $k_\tau$, $k_\mu$ are correction factors. Such a PAMR fitting algorithm can be extended to include the PAMR measurements from all other electrodes. To determine the desired initial fitting parameters—the fitting function $f_\tau$ for the THR and $f_\mu$ for the MCL—a priori data from a large pool of patients can be used where behavioural determined fittings done by an expert are available together with the PAMR measurement. The PAMR measurement module then repeats the measurement process for each remaining electrode channel, step 206.

Figure 3:
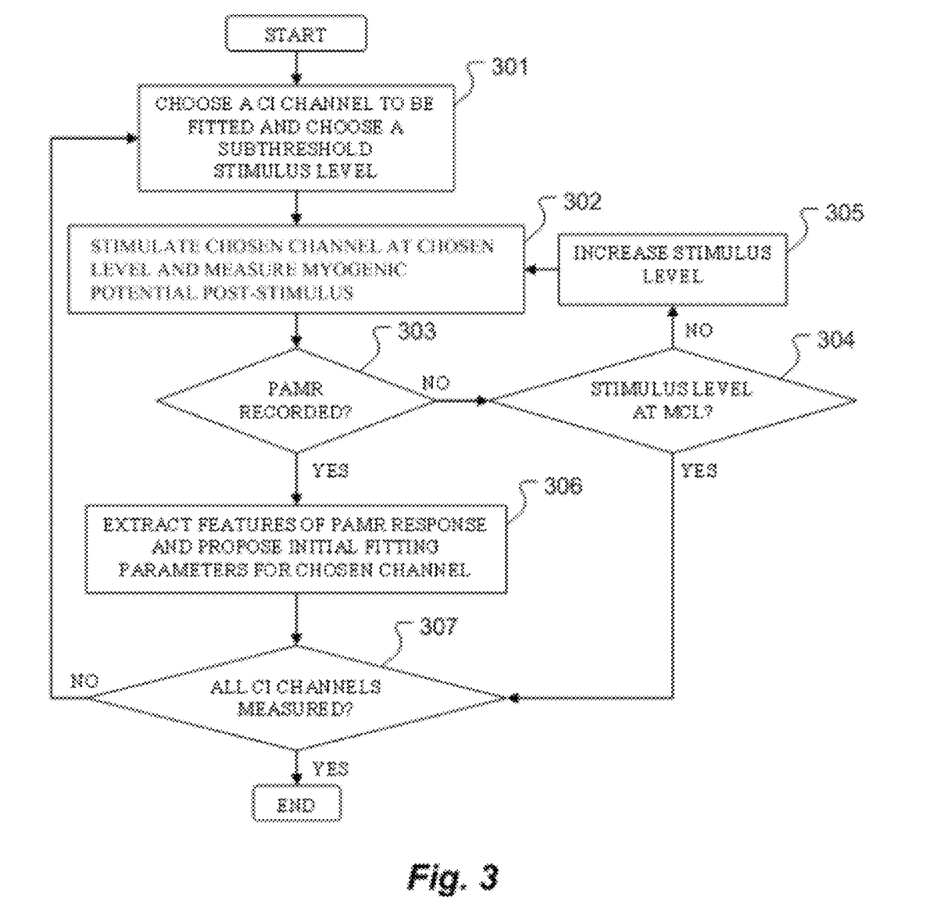
FIG. 3 shows various logical steps in a PAMR-based patient fit process according to another embodiment of the present invention.

FIG. 3 shows an example of another PAMR threshold-based fitting procedure using the PAMR characteristics (such as threshold, peak-to peak amplitude, latencies) for each hearing prosthesis channel to determine the operating values (e.g., THR and/or MCL) of the respective electrode channel. The PAMR measurement module selects an initial electrode channel to be fit, step 301.

In an iterative process, the PAMR measurement module then stimulates the current electrode channel at the chosen stimulus level and the myogenic potential is measured and recorded post-stimulus, step 302. The initial stimulation level should be sub-threshold (e.g. 0 cu) and if no PAMR response is measured (303) and the stimulus level is still below the user's MCL, step 304, the stimulus level is increased, step 305 and the measurement repeated, step 302, until a PAMR response is obtained, step 303.

Using the stimulation level at which the first PAMR response was observable (PAMR-THR) together with PAMR waveform features like the latency of the peaks (PAMR-P1, PAMR-N1, . . . ), fitting functions THR=$f_\tau$(PAMR-THR, PAMR-P1, PAMR-N1, . . . ) and MCL=$f_\mu$(PAMR-THR, PAMR-P1, PAMR-N1, . . . ) can be approximated, step 306. For example, this may be based on a spline interpolation technique (see, for example Bojanov et al., *Spline Functions and Multivariate Interpolations*, Kluwer Academic Publishers, Dordrecht/Boston/London, 1993; incorporated herein by reference). Another approach may make a determination of the THR as PAMR-THR times some fit factor x and MCL as PAMR-THR times some fit factor y may be sufficient for some embodiments. An alternative embodiment may be able to estimate the THR and MCL using a single PAMR waveform feature, for example THR=$k_\tau$*PAMR-THR and MCL=$k_\mu$*PAMR-THR where $k_\tau$, $k_\mu$ are correction factors. Such a PAMR fitting algorithm can be extended to include the PAMR measurements from all other electrodes. To determine these desired initial fitting parameters—i.e. the fitting function $f_\tau$ for the THR and $f_\mu$ for the MCL—a priori data from a large pool of patients can be used where behaviourally determined fittings done by an expert are available together with the PAMR measurement. The process is then repeated for each remaining electrode channel, step 307.

Figure 4:
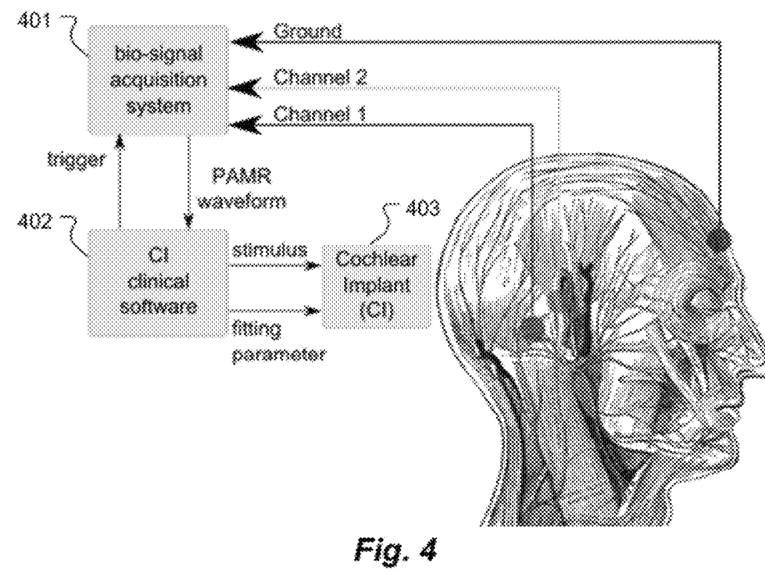
FIG. 4 shows various devices in a system for performing a PAMR-based patient fit using an external bio-signal acquisition system.
Figure 5:
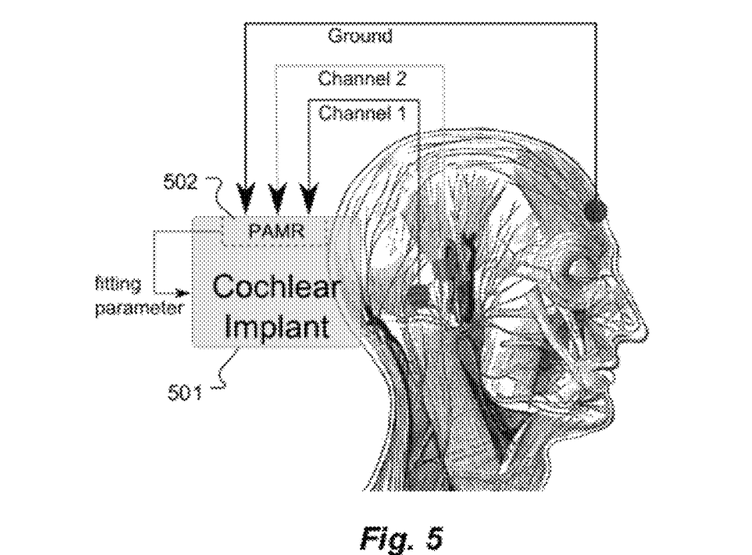
FIG. 5 shows a system for performing a PAMR-based patient fitting with a fit module internal to the hearing prosthesis.

FIG. 4 shows various devices in a PAMR measurement module for performing a PAMR-based fit using an external bio-signal acquisition system. CI clinical patient fitting module software 402 controls the fit process sending electrical stimulus signals to each electrode channel in the cochlear implant 403 during the fit process, as well as the THR and MCL fitting parameters as determined by the PAMR measurements of the external bio-signal acquisition system 401 such as an Electroencephalography (EEG) or Electromyography (EMG) recording system. The patient fitting module software 402 triggers the CI stimulus and PAMR measurement, imports the PAMR waveform, and derives the new fitting parameters, THR and MCL. FIG. 5 shows an example of another system for performing a PAMR-based fitting with a PAMR fit module 502 that is internal to the hearing prosthesis 501. In another embodiment, a PAMR fit module may be implemented in the external audio processor (e.g., BTE processor).

Figure 6:
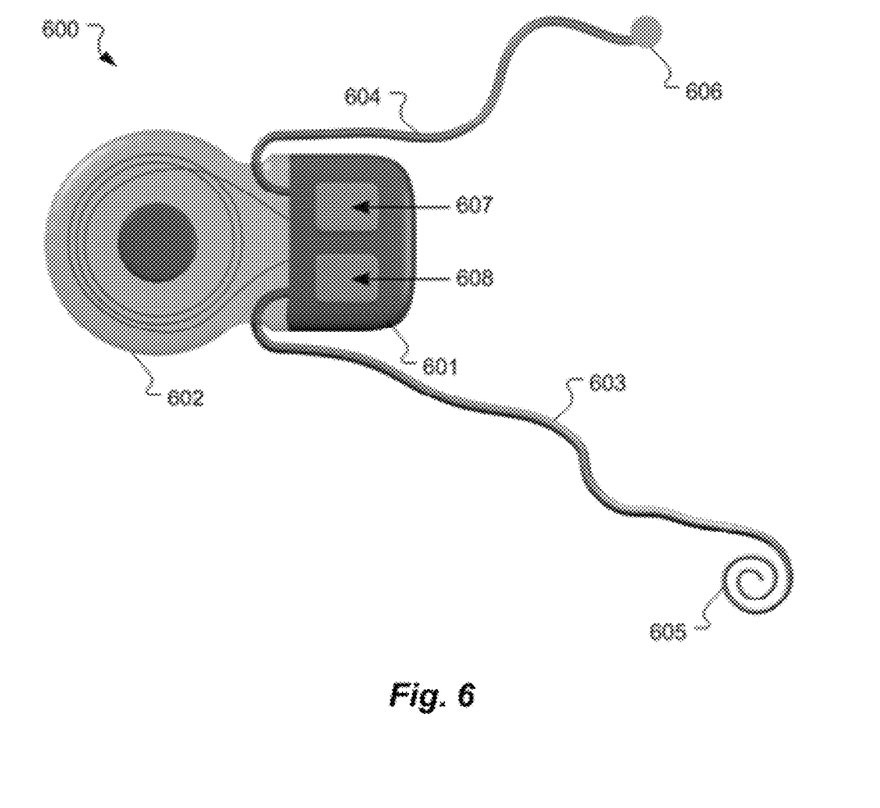
FIG. 6 shows an example of implantable components of a cochlear implant system adapted for performing a PAMR-based patient fitting process.
Figure 7:
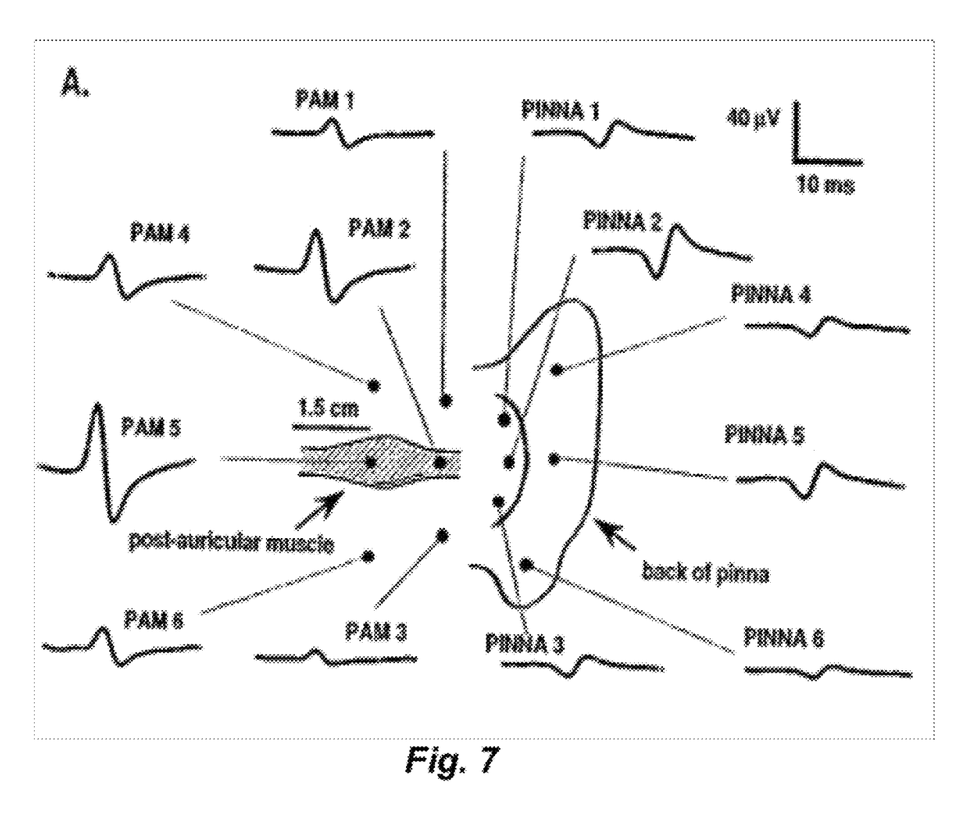
FIG. 7 illustrates various different possible measurement electrode positions.

FIG. 6 shows an example of a cochlear implant 600 adapted for electing and/or recording PAMR. Readily apparent are the usual components of a cochlear implant 600 including an implant processor 601 coupled to a receiver coil 602 that communicates data and power signals with external components. The implant processor responds to incoming communications signals by delivering electrode stimulation signals via an electrode lead 603 to the electrode contacts 605 within the cochlea. The outer surface of the implant processor 601 includes a reference contact 608 for the electrode stimulation signals. A separate PAMR lead 604 terminates in a PAMR recording electrode 606 that ends at the post auricular muscle. FIG. 7 shows various possible implanted positions for the PAMR recording electrode 606 (based on FIG. 3A from O'Beirne & Patuzzi (1999)). In some embodiments, the PAMR recording electrode 606 may be implemented as an array of electrode contacts. A separate PAMR reference electrode 607 also is present on the outer surface of the implant processor 601. The PAMR reference electrode 607 may also be remotely placed.

Figure 8:
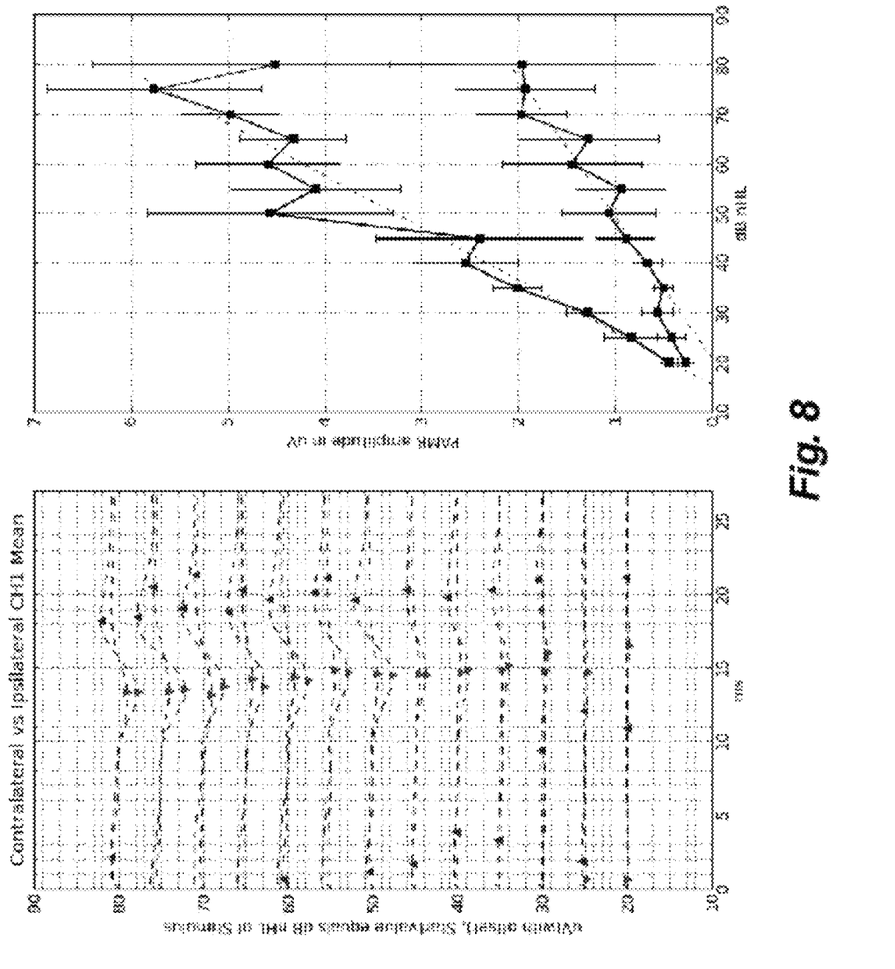
FIG. 8 shows a graph of data from a PAMR amplitude growth sequence according to one set of experiments.

FIG. 8 shows a graph of data from a PAMR amplitude growth sequence according to one set of experiments using an active chin-on-chest posture of the patient. The left plot shows the single PAMR waveforms for different stimulation amplitudes for an ipsilateral and a contralateral recording. The right plot shows the amplitude growth function of the PAMR amplitude for the two recording sides. The dotted lines represent the slope of a linear fit of the respective data. Measurements were based on 100 μs clicks measuring 20-80 dB nHL in steps of 5 dB. An interleaved sequence was used of 4 iterations with each signal repeated 30 times per iteration, and ipsilateral left ear stimulus, left PAM, and contralateral right ear stimulus, left PAM. A PAMR amplitude growth sequence was measured in a normal hearing subject using an eyes front or side as well as sucking condition for several stimulation levels. A clear increase in PAMR amplitude with increasing stimuli level is observable.

Figure 9:
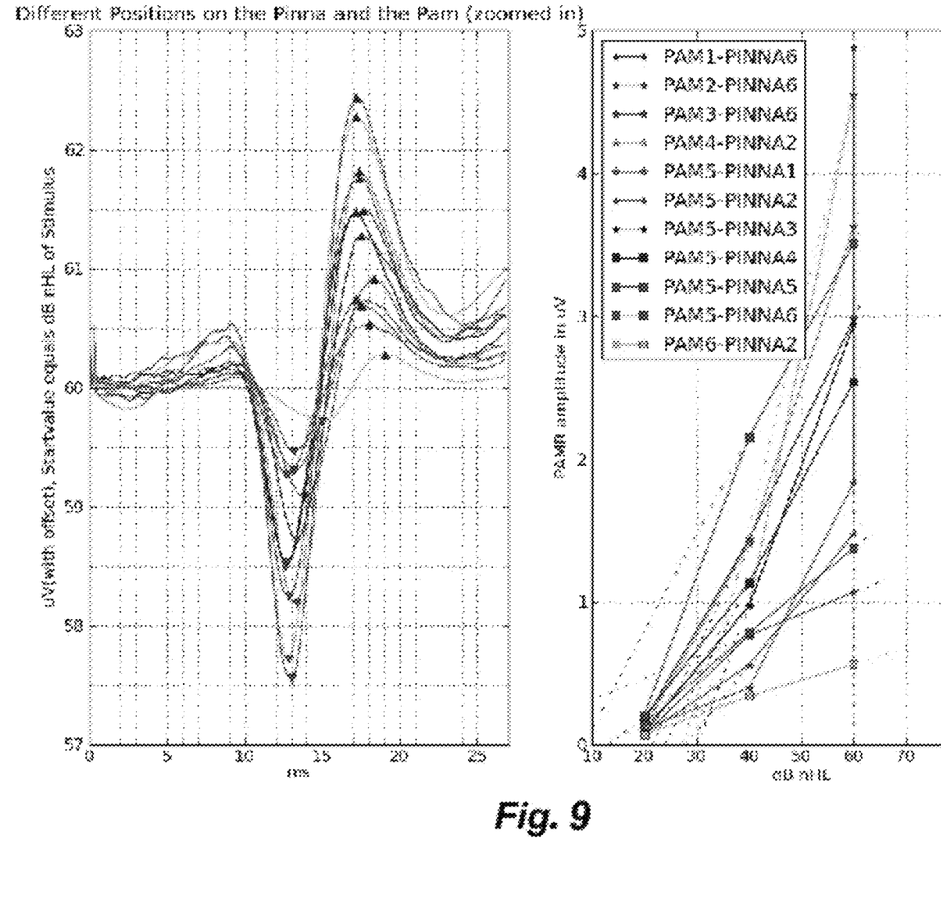
FIG. 9 shows a graph of data from PAMR responses from one set of experiments for different measurement electrode positions of the same subject.

FIG. 9 shows a graph of data from a set of experiments in the same patient measuring PAMR responses for different measurement electrode positions (such as in FIG. 7). The graphed data shows that the PAMR threshold is independent of the electrode position. The left plot shows the single PAMR waveforms for the different electrode positions. The right plot shows different amplitude growth function of the PAMR amplitude. The dotted lines represent the slope of a linear fit of the respective data.

Figure 10:
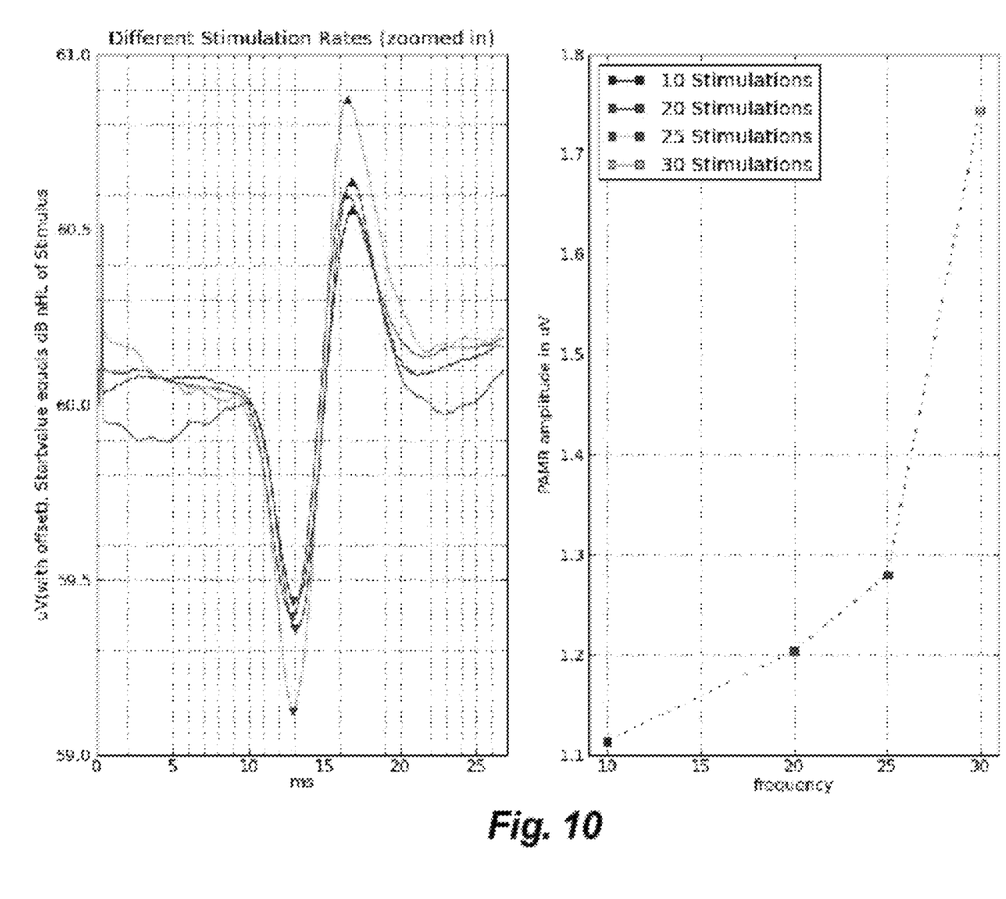
FIG. 10 shows a graph of data showing PAMR responses from one set of experiments for different repetition rates.

FIG. 10 shows a graph of data from a set of experiments in one patient measuring PAMR responses at 60 dB nHL for different repetition rates. The right plot shows the PAMR amplitude over stimulation rate. The left plot shows the single PAMR waveforms for the different stimulation rates. The PAMR response may be determined for different stimulation rates and the obtained information about the auditory system can be used to derive THR=ft( ) and MCL=fm( ) for different coding strategies and their parameters such as pulse-rate. One determination of THR and MCL at different stimulation rates may be based on the measured integration effect of the PAMR response as shown in FIG. 10. The stimulation rate may preferably be higher than 20 Hz or 25 Hz or 30 Hz, and the preferred time-lag between stimulation pulse and measurement may be 10-25 ms for acoustically-evoked PAMR and 5-20 ms for electrically-evoked PAMR.

As the efferent pathway of the post-auricular muscle reflex (PAMR) is similar to the stapedius muscle reflex (SRT), a similar high correlation with the MCL fittings parameter of the hearing prosthesis and a similar high percentage of hearing prosthesis users where the PAMR is recordable is expected. Moreover, while the eSRT measurement (for example) only gives information about the MCL fitting value, the amplitude growth sequence of the PAMR response also should correlate with the THR fitting value. By analyzing the differences of the eCAP amplitude growth sequence with the ePAMR amplitude growth sequence further insight into the auditory system between the auditory nerve and the higher auditory pathway is expected due to its different sites of generation.

Due to the relatively large myogenic response, a reduced number of measurement repetitions will be needed to obtain a reliable recording of the PAMR response. This results in a short measurement time—about 30 measurements per second are possible and with an assumed minimum of N=10 repetitions per CI channel and stimulation level, for example for a 12 channel CI an amplitude growth sequence with 5 stimulation levels has a total measurement time of minimal 20 seconds. To account for such things as adaptation effects, a reduced number of measurements per second might be needed and also a permutation of the stimulation levels and electrodes is favorable.

Figure 11:
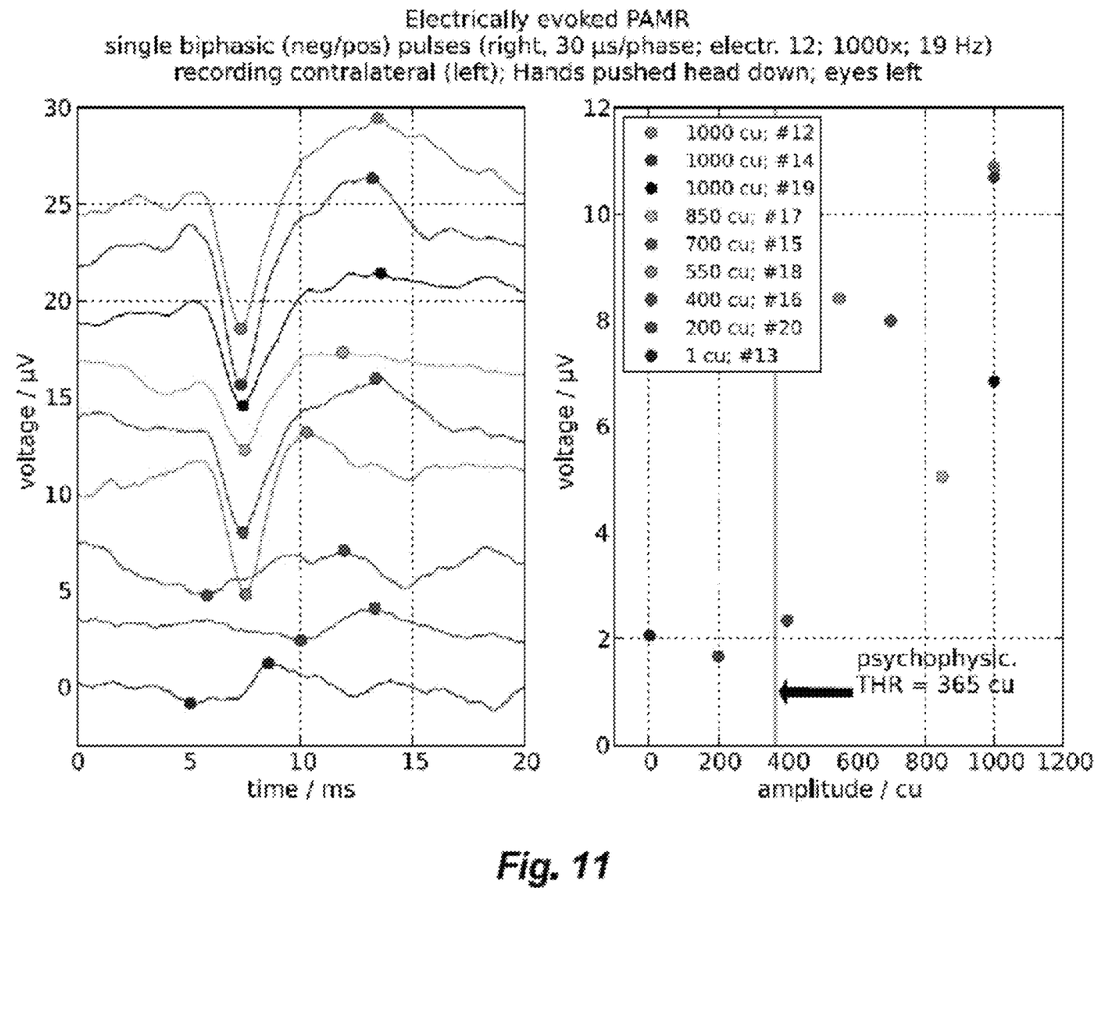
FIG. 11 shows an example of an ePAMR amplitude growth function measured with a specific user.

Measuring the PAMR is relatively easy using three recording electrodes and any existing EEG recording system that is available in most clinics. The patient can be awake, and for children where objective measures are most needed, simple suckling/eating movement can be used instead of an exhausting eye movement as proposed by Purdy et al. (2005). Moreover, the PAMR is not affected by the development of the postauricular muscle, i.e. microtia (Takagi et al. 1984). And in contrast to mid- and long-latency event-related brain potentials, the PAMR is not affected by the attention of the subject (Hackley et al. 1987). It is possible that anesthesia during surgery might reduce or stop the PAMR, but further research is needed as it might also be possible that due to its size a PAMR can be obtained during surgery. FIG. 11 shows an example of an ePAMR amplitude growth function measured with a MED-EL PULSAR ci100 user. The ePAMR threshold was at 400 current units (cu) and the behavioral threshold was at 365 cu.

So adding a new objective measure for fitting a hearing prosthesis system based on PAMR is expected to increase the quality of the fitting and overcome many of the limitations of the existing objective fit methods. This especially reflects that the PAMR as a top-down event which implicates a major portion of the auditory pathway. That is, higher auditory processes like loudness summation are included, in contrast to, for example, eCAP measurements where only the peripheral part of the auditory system is observed.

Embodiments of the invention may be implemented in whole or in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

For example, a pseudo code representation of a generic embodiment might be set forth as follows:
Process PatientFitting
determine PAMR response to auditory stimulus
set operating parameter (maplaws/THR/MCL) based on PAMR response Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. An implant fitting arrangement for fitting a cochlear implant system to a cochlear implant patient, the arrangement comprising:
   a PAMR measurement module configured to:
      i. apply an electrical stimulus signal to an electrode contact of a cochlear implant electrode array implanted within the cochlea of the patient, and
      ii. determine a post-auricular muscle reflex (PAMR) response of the patient to the electrical stimulus signal; and
   a patient fitting module configured to set an operating characteristic of the cochlear implant system based on the PAMR response.

2. An implant fitting arrangement according to claim 1, wherein the PAMR response includes a PAMR amplitude growth function and wherein the patient fitting module is configured to set the operating characteristic to include an output compression function based on the PAMR amplitude growth function.

3. An implant fitting arrangement according to claim 1, wherein the PAMR measurement module is configured to determine a PAMR response that includes a PAMR threshold stimulus level at which a PAMR is measured in the patient.

4. An implant fitting arrangement according to claim 1, wherein the patient fitting module is configured to set an operating characteristic that includes a lowest stimulation level (THR) that elicits an audible percept in the patient.

5. An implant fitting arrangement according to claim 1, wherein the patient fitting module is configured to set an operating characteristic that includes a maximum comfort level (MCL) beyond which the audible precept in the patient is uncomfortably loud.

6. An implant fitting arrangement according to claim 1, wherein the PAMR measurement module is configured to determine a PAMR response based on an iterative stimulus process.

7. An implant fitting arrangement according to claim 1, wherein the PAMR measurement module is configured to determine a PAMR response based on an external bio-signal acquisition system.

8. An implant fitting arrangement according to claim 1, wherein the PAMR measurement module is configured to determine a PAMR response based on an internal fit module in an implanted stimulation processor.

9. An implant fitting arrangement according to claim 1, wherein the PAMR measurement module is configured to determine a PAMR response based on an artifact reduction algorithm.

10. An implant fitting arrangement according to claim 1, wherein the PAMR measurement module is configured to determine a PAMR response using a permuted stimulus level to account for bias related to slowly varying muscle tonicity.

11. An implant fitting arrangement according to claim 1, wherein the PAMR measurement module is configured to determine a PAMR response on one side, either ipsilateral or contra-lateral, of the patient.

12. An implant fitting arrangement according to claim 1, the PAMR measurement module is configured to determine a PAMR response on both sides of the patient.

13. An implant fitting arrangement according to claim 1, wherein the PAMR measurement module is configured to determine a PAMR response during a controlled post-auricular muscle contraction of the patient or during a controlled jaw movement of the patient.

14. An implant fitting arrangement according to claim 1, wherein the PAMR measurement module is configured to determine a PAMR response while the patient performs a sucking action or while the chin of the patient is positioned against their chest.

15. An implant fitting arrangement according to claim 1, wherein the patient fitting module is configured to set an operating characteristic associated with the electrode contact in the implanted electrode array.

16. An implant fitting arrangement according to claim 15, wherein the electrical stimulus signal includes a single electrode burst signal.

17. An implant fitting arrangement according to claim 15, wherein the electrical stimulus signal includes a multi-electrode burst signal.

18. A method of fitting a cochlear implant system to a cochlear implant patient, the method comprising:
- applying an electrical stimulus signal to an electrode contact of a cochlear implant electrode array implanted within the cochlea of the patient,
- determining a post-auricular muscle reflex (PAMR) response of the patient to the electrical stimulus signal; and
- setting an operating characteristic of the cochlear implant system based on the PAMR response.

19. A computer program product encoded in a non-transitory computer-readable medium for fitting a cochlear implant system to a cochlear implant patient, the product comprising:
- program code for applying an electrical stimulus signal to an electrode contact of a cochlear implant electrode array implanted within the cochlea of the patient;
- program code for determining a post-auricular muscle reflex (PAMR) response of the patient to the electrical stimulus signal; and
- program code for setting an operating characteristic of the cochlear implant system based on the PAMR response.

* * * * *